United States Patent
Schneider et al.

[11] Patent Number: 5,906,726
[45] Date of Patent: May 25, 1999

[54] ELECTROCHEMICAL SENSOR APPROXIMATING DOSE-RESPONSE BEHAVIOR AND METHOD OF USE THEREOF

[75] Inventors: Alan A. Schneider, Wexford; Brian K. Davis; Towner B. Scheffler, both of Butler, all of Pa.

[73] Assignee: Mine Safety Appliances Company, Pittsburgh, Pa.

[21] Appl. No.: 08/887,067

[22] Filed: Jul. 2, 1997

Related U.S. Application Data

[63] Continuation-in-part of application No. 08/616,689, Mar. 15, 1996, Pat. No. 5,667,653.

[51] Int. Cl.$^6$ .................................................. G01N 27/404
[52] U.S. Cl. .................... 205/775; 204/406; 204/415; 204/432; 205/782.5; 205/785.5; 205/786.5
[58] Field of Search .................... 204/415, 431, 204/432, 406; 205/782.5, 783, 785.5, 786.5, 775

[56] References Cited

U.S. PATENT DOCUMENTS

| | | | |
|---|---|---|---|
| 4,297,689 | 10/1981 | Shan et al. | 340/632 |
| 4,329,214 | 5/1982 | Spritzer et al. | 204/431 |
| 4,407,291 | 10/1983 | Hagihara et al. | 204/415 |
| 4,627,906 | 12/1986 | Gough | 204/415 |
| 5,667,653 | 9/1997 | Schneider et al. | 204/431 |

FOREIGN PATENT DOCUMENTS

| | | |
|---|---|---|
| 0126623 | 11/1984 | European Pat. Off. |
| 2288875 | 11/1995 | United Kingdom |

*Primary Examiner*—T. Tung
*Attorney, Agent, or Firm*—James G. Uber; Henry E. Bartony, Jr.

[57] ABSTRACT

The present invention provides an electrochemical sensor for the detection of an analyte, wherein the output or response of the electrochemical sensor approximates the dose-response behavior of a living organism upon exposure to the analyte. The electrochemical sensor comprises a housing including an inlet port therein to allow the analyte to enter the housing. The electrochemical sensor further comprises at least a first electrode and a second electrode within the housing. Electrical conductivity is maintained between the first electrode and the second electrode via an electrolyte system present within the housing. The electrochemical sensor further comprises a resistor in series electrical connection with the first electrode and the second electrode. This resistor has a resistance adapted to be sufficiently high such that the output of the electrochemical sensor over time at a particular concentration of the analyte approximates the response of a living organism to the analyte over time at that particular concentration. The present invention also provides a method of using an electrochemical sensor as describe above.

35 Claims, 7 Drawing Sheets

ELECTROCHEMICAL SENSOR APPROXIMATING DOSE-RESPONSE BEHAVIOR AND METHOD OF USE THEREOF

RELATED REFERENCE

The present application is a continuation-in-part application of U.S. patent application Ser. No. 08/616,689 filed Mar. 15, 1996, now U.S. Pat. No. 5,667,653, the disclosure of which is incorporated herein by reference.

FIELD OF THE INVENTION

The present invention relates to an electrochemical sensor for detecting a chemical analyte, and, particularly, to an electrochemical sensor exhibiting a response approximating a dose-response curve of a living organism upon exposure to the chemical analyte.

BACKGROUND OF THE INVENTION

Electrochemical sensors are widely used to determine electroactive chemical species in liquid, gas and vapor phases. Electrochemical sensors or cells in which measurable current flows can be conveniently classified as galvanic when operated to produce electrical energy and electrolytic when operated at a constant potential via consumption of electrical energy from an external source. Many electrochemical sensors can be operated in either a galvanic or an electrolytic mode. A comprehensive discussion of electrochemical gas sensors is also provided in Cao, Z. and Stetter, J. R., "The Properties and Applications of Amperometric Gas Sensors," *Electroanalysis*, 4(3), 253 (1992), the disclosure of which is incorporated herein by reference.

In a typical electrochemical sensor, the chemical entity to be measured (the "analyte") typically diffuses from the test environment into the sensor housing through a porous or permeable membrane (through which the analyte is mobile, but through which the electrolyte is not mobile) to a working electrode (sometimes called a sensing electrode) wherein the analyte chemically reacts. A complementary chemical reaction occurs at a second electrode in the sensor housing known as a counter electrode (or an auxiliary electrode). The electrochemical sensor produces an analytical signal via the generation of a current arising directly from the oxidation or reduction of the analyte at the working and counter electrodes.

In general, the electrodes of an electrochemical sensor provide a surface at which an oxidation or a reduction reaction occurs (that is, an electrochemically active surface) to provide a mechanism whereby the ionic conduction of an electrolyte solution in contact with the electrodes is coupled with the electron conduction of each electrode to provide a complete circuit for a current. By definition, the electrode at which an oxidation occurs is the anode, while the electrode at which the "complimentary" reduction occurs is the cathode.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte over the concentration range of interest.

As discussed above, the electrical connection between the working electrode and the counter electrode is maintained through an electrolyte. The primary functions of the electrolyte are: (1) to efficiently carry the ionic current; (2) to solubilize the analyte; and (3) to support both the counter and the working electrode reactions. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

In current electrochemical sensors, every effort is generally made to achieve a quick response time. The response time is typically defined as the amount of time an electrochemical sensor must be exposed to a particular concentration of an analyte before an accurate measurement of that concentration can be made by the electrochemical sensor. The response of a living organism (for example, the human body) to certain chemicals, however, is often a very complicated function of time of exposure, the concentration of the chemical in the environment, and other factors. The uptake of or concentration of a chemical (or the concentration of a reaction product resulting from exposure to such a toxic chemical) in the human body is often expressed as a dose-response curve which sets forth such concentration as a function of time for specific environmental exposure concentrations. Over a broad range of environmental concentrations, a substantial amount of exposure time may be required before any adverse effect is experienced. In general, the higher the environmental concentration of a chemical, the shorter the exposure time required to experience adverse effects. Current electrochemical sensors cannot model the dose-response behavior of a living organism upon exposure to a chemical.

It is very desirable to develop electrochemical sensors capable of providing a response which approximates the dose-response behavior of a living organism upon exposure to a chemical, and, particularly a toxic chemical.

SUMMARY OF THE INVENTION

In general, the present invention provides an electrochemical sensor for the detection of an analyte, wherein the output or response of the electrochemical sensor approximates the dose-response behavior of a living organism upon exposure to the analyte. The electrochemical sensor comprises a housing including an inlet port therein to allow the analyte to enter the housing. The electrochemical sensor further comprise at least a first electrode and a second electrode within the housing. Electrical conductivity is maintained between the first electrode and the second electrode via an electrolyte system present within the housing.

The electrochemical sensor further comprises a resistor in series electrical connection with the first electrode and the second electrode. This resistor has a resistance sufficiently high such that the output of the electrochemical sensor over time at a particular concentration of the analyte approximates the response of a human body to the analyte over time at that particular concentration.

The resistance required to achieve such an output is dependent upon the apparent area of the first or working electrode (for example $\pi r^2$, wherein r is the radius of a generally circular working electrode). In general, the resistance is approximately inversely linearly related to the apparent area of the working electrode. For a desired output the product of the required resistance and the apparent area of the working electrode will remain approximately constant. Preferably, the product of resistance and the apparent area of the working electrode is at least approximately 1 $k\Omega \cdot cm^2$. Thus, for a working electrode having an apparent area of 1 $cm^2$, the resistor preferably has a resistance of at least 1 $k\Omega$. For a working electrode having an apparent area of 2 $cm^2$, the resistor preferably has a resistance of at least 0.5 $k\Omega$. More preferably, the product of the resistance and the apparent area of the working electrode is at least approximately 10 $k\Omega \cdot cm^2$. Most preferably, the product of the resistance and the apparent area of the working electrode is at least approximately 50 $k\Omega \cdot cm^2$. The apparent area of the second electrode or counter electrode is preferably sufficiently large such that the counter electrode does not move significantly in voltage under the current required to react the analyte at the working electrode.

The electrochemical sensor preferably further comprises an alarm mechanism to provide an alarm signal when the output of the sensor reaches a predetermined value. The electrochemical sensor also preferably further comprises reset circuitry to reset the electrochemical sensor after an alarm is signaled to end the alarm signal and once again allow the electrochemical sensor to detect the analyte. In one embodiment, the reset circuitry is adapted to substitute a second resistor having a lower resistance than the first resistor into electrical connection between the first electrode and the second electrode for a period of time. The reset function can be initiated, for example, by the user pressing a reset button.

The present invention also provides a method of using an electrochemical sensor as described above. The method comprises the steps of:

a. placing the electrochemical sensor in communicative connection with an environment containing the analyte such that the analyte can react at the working electrode;

b. measuring the output of the electrochemical sensor to obtain a measurement of the concentration of the analyte in the environment.

Measuring the output of the electrochemical sensor may, for example, comprise the step of measuring the current flow between the working electrode and the counter electrode.

Preferably, the method further comprises the step of providing an alarm signal if the measured current flow reaches a predetermined value. The method also preferably further comprises the step of resetting the electrochemical sensor after an alarm is signaled to end the alarm signal and once again allow the electrochemical sensor to detect the analyte. Resetting the electrochemical sensor may, for example, comprise the step of substituting a second resistor having a lower resistance than the first resistor into electrical connection between the first electrode and the second electrode for a period of time.

In currently available electrochemical sensors the electrical resistance between the working electrode and the counter electrode is maintained as low as possible. Load resistances may be used in electrolytic electrochemical sensors to smooth noisy signals, but such load resistances are generally maintained at or below 50 $\Omega$. Indeed, the slowed response times and increased complication of electrochemistry associated with relatively large load resistances across an electrochemical sensor were (before the present invention) believed to be highly undesirable. However, applicants have discovered that by adjusting the load resistance used with/across a sensor, response times can be adjusted to approximate dose/response curves such as those established for toxic gases, for example, carbon monoxide (CO). In general, applicants have discovered that by increasing the load resistance across an electrochemical sensor to levels above those commonly used in current electrochemical sensors, sensor response is slowed and a plot of analyte concentration versus response time conforms to dose/response curves for toxic agents. It is very surprising that increasing the load resistance across a sensor provides a desirable result.

The surprising results of the present invention lead to a very simple and, therefore, inexpensive measuring circuit based, for example, on a simple alarm set point value. In that regard, the sensors of the present invention modulate the response times to fit a dose/response curve without the necessity of external algorithms or complicated measuring circuitry. The results achieved through the increased load of the present invention can be achieved in a variety of electrochemical reactions in aqueous or nonaqueous electrolytes. The electrolyte can be acidic or caustic.

The electrochemical sensors of the present invention are particularly useful for the detection of CO and the approximation of human dose-response curves established for exposure to various concentrations of CO. Moreover, the simple and inexpensive electronics of the electrochemical sensors of the present invention help to reduce the costs of CO detectors incorporating such sensors, opening the way for use of such CO detectors in the home.

The cost of the electrochemical sensors of the present invention can be further reduced through use of metallic housings encasing common acidic electrolyte systems. Although neither the fabrication materials of the sensor housing nor the acidic or basic nature of the electrolyte system are of great importance to the operation of the electrochemical sensors of the present invention, small, low-cost electrochemical sensors have been fabricated with common acidic electrolyte systems enclosed within a metallic housing (for example, steel). Acid systems, such as aqueous solutions of sulfuric acid ($H_2SO_4$) and phosphoric acid ($H_3PO_4$) satisfy the criteria set forth above for electrolytes very well and are, therefore, commonly used as electrolytes in electrochemical sensor. As used herein, the term "acidic electrolyte system" refers generally to any electrolyte system having a pH less than 7.0.

It is extremely surprising and contrary to the understanding in the art that a metal, and, particularly steel, is suitable for use as a housing in an electrochemical sensor which contains an acidic electrolyte. An obvious concern is corrosion of the metallic housing by the acidic electrolyte, leading to sensor failure. Another concern is erratic sensor performance arising from the electrical currents associated with corrosion. However, it has been discovered that such corrosion and associated currents do not preclude the use of a metallic housing in electrochemical sensors containing acidic electrolyte systems. The metallic housings of the present invention operate well even at a pH less than approximately 3.0. Indeed, the metallic housing of the present invention even operate at a pH less than approximately 1.0.

Metal housings provides numerous advantages over electrochemical sensors using conventional plastic housings. For example, metallic housings are significantly less expensive to manufacture than injection molded plastic housings. Also, metal housings can be fabricated to be much thinner than plastic housings because metals exhibit greater resistance to cracking and, therefore, leaking, than plastics of a similar thickness. In other words, to achieve the same degree of ruggedness in a plastic housing as is achieved in a metallic housing, a much thicker encasement is generally needed in the plastic housing.

In that regard, plastic housings must be at least approximately 100 mil in wall thickness for use in electrochemical sensor housings, whereas the wall thickness of the metallic housings used in the electrochemical sensors of the present invention can be as little as approximately 5 mil (for example, in the case of stainless steel). Clearly, metallic housings enable the fabrication of much smaller electrochemical sensors than previously possible using plastic housings. Indeed, using metallic housings, electrochemical sensors as small as approximately 20 mil (approximately 0.51 mm) in total height are possible using electrodes known in the art. Detectors and instruments incorporating such sensors can, therefore, be fabricated to be much smaller in size than currently possible.

Moreover, unlike plastics, metals are generally impermeable to gases. Therefore, the problems of erratic response and high baseline currents experienced with existing plastic-housing designs is substantially eliminated by the present invention. The gas permeability of the plastic grommet used in one embodiment of the present invention is negligible because of the limited size of the grommet.

Further, because of the relatively high thermal conductivity of metals (as compared to plastics), sensors comprising metallic housings reach thermal equilibrium much more rapidly with changes in environmental temperature. This rapid thermal equilibration results in smaller temperature gradients across the sensor, leading to more predictable performance. Still further, the use of metal housings rather than plastic housings substantially eliminates the radio frequency (RF) interference concerns that may arise with the use of plastic housings.

DETAILED DESCRIPTION OF THE INVENTION

The efficacy of the electrochemical sensors of the present invention is discussed below in connection with the operation of an electrochemical sensor in the galvanic mode for the detection of CO. In the case of a sensor for the detection of carbon monoxide, the electrochemically active surfaces of both the working electrode and the counter electrode preferably comprised a platinum (Pt) electrocatalyst. In such a sensor, CO is oxidized at the anodic working electrode, while the complimentary (that is, reduction) reaction occurs at the cathodic counter electrode. The appropriate half-cell reactions for the present CO sensor are as follows:

$$CO + H_2O \rightarrow CO_2 + 2H^+ + 2e^-$$

$$\tfrac{1}{2}O_2 + 2H^+ + 2e^- \rightarrow H_2O$$

The above half-cell reactions (for the working electrode and the counter electrode, respectively) result in the following overall cell reaction.

$$CO + \tfrac{1}{2}O_2 = CO_2$$

An important application for electrochemical sensors of the present invention is CO detection in the home. In that regard, CO is a very toxic gas that can quickly reach lethal concentrations in a home environment from numerous sources including a malfunctioning gas range or a malfunctioning furnace. Specifications for CO detectors for home use have been established by Underwriters Laboratories, Inc. (UL). The UL specifications for home CO detectors require generally that the CO detector respond before predetermined time intervals for specific CO concentrations. In general, the higher the CO concentration, the faster the required response time.

Underwriters Laboratories Specifications

Figure 1:
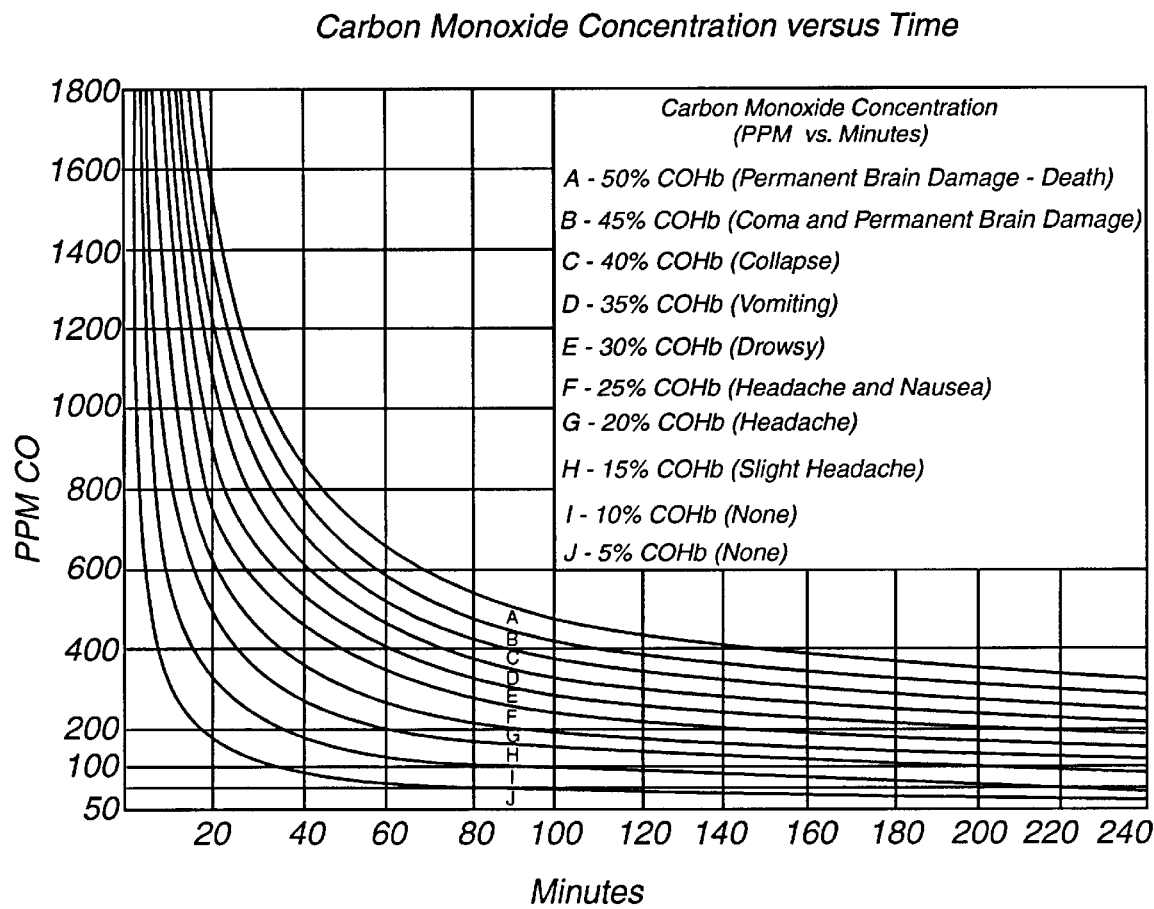
FIG. 1 provides a guideline for CO detector performance as set forth in UL Standard No. 2034.

The specifications for CO detectors are set forth in UL Standard No. 2034 (the UL Standard) and were established based upon the concentration of CO in the blood and the corresponding effect such concentration has on the human physiology. The concentration of CO in the blood is expressed as a percentage of carboxyhemoglobin (designated % COHb), a complex that forms as CO enters the blood stream. The % COHb is a function of the concentration of CO in the environment and the time of exposure. FIG. 1, taken form UL Standard No. 2034, provides a basis for the guidelines for CO detector performance.

Because % COHb is a complicated function of the time of exposure, the concentration of CO, and the work effort exerted by the person exposed, UL determined that it would be clearer to indicate parts per million (ppm) CO over time rather than % COHb. The specific relation between the concentration of CO and COHb is provided in a short form equation in the UL Standard.

Under the UL specifications, a CO detector must operate at or below the 10% COHb curve (designated by the letter "I" in FIG. 1). Three concentrations are tested, and the detector must exhibit an alarm signal within the maximum times set forth in Table 1 for the corresponding CO concentration.

TABLE 1

| Co Concentration (ppm) | Maximum Response Time (minutes) |
|---|---|
| 100 | 90 |
| 200 | 35 |
| 400 | 15 |

To reduce the number of "false" alarms at relatively safe, low exposures to CO, the UL Standard includes false alarm resistance specifications. In that regard, the detector must not signal an alarm below the 2.5% COHb level (this curve is not shown in FIG. 1—see Table 2 below). As shown in Table 2, three concentrations are tested, and the CO detector must not exhibit an alarm before the minimum exposure times for the corresponding CO concentrations.

TABLE 2

| Co Concentration (ppm) | Exposure Time |
|---|---|
| 100 ± 5 | 16 minutes |
| 60 ± 3 | 28 minutes |
| 15 ± 3 | 30 days |

Moreover, the CO detector must be equipped with an alarm reset button which silences the alarm signal and resets the detector to once again sense CO. If the CO concentration remains at 100 ppm or greater, the detector must exhibit the alarm signal again within five minutes after the reset button is activated.

Sensor Fabrication

In the present studies, electrochemical sensors 10 (see FIG. 2A) comprising a metallic housing was used. The interior of such metallic housings was filled with an acidic electrolyte such as $H_2SO_4$. Acid electrolyte systems suitable for use in the such metallic housings can take many forms. For example, a liquid electrolyte can be absorbed on a solid support such as glass fiber or granular $SiO_2$. A gelled acidic electrolyte (for example, fine silica with $H_2SO_4$) can also be used. Likewise, solid acids such as tungstic acid ($H_2WO_4$), molybdic acid, acidic Nafion™ polymer and acidic Flemion™ polymer are also suitable for use in the present invention.

In general, it has been discovered that metals for use in electrochemical sensors comprising acidic electrolyte systems must be sufficiently "corrosion resistant" (in the electrolyte systems contained therein) that the ratio of the output signal (current) to the corrosion current is sufficiently great to distinguish between concentration levels of the analyte over the concentration range of interest. Preferably, the maximum corrosion current is no greater than one half of the output signal current resulting from the reaction of the analyte at the lowest detectable concentration. Corrosion currents are easily measurable using any of a number of commercially available instruments such as a potentiostat and/or galvanostat. For example, a Model 273 Potentiostat/Galvanostat available from EG&G Princeton Applied Research of Princeton, New Jersey can be used in connection with Model 341 Softcorr Corrosion Measurement Software also available from EG&G Princeton Applied Research. The corrosion currents can easily be determined for a particular electrochemical sensor in the absence of electrochemical reaction of the analyte.

Generally, metals for use in the metallic housings used in the present invention preferably have a maximum corrosion rate no greater than approximately 1 mil/year (one mil equals 0.001 in) in the acidic electrolyte system at operating potential and at temperatures of approximately 50° C. or less. As used herein, the phrase "maximum corrosion rate" refers to the highest rate of corrosion at any point over the surface of the metal housing. Metal suppliers commonly meet such maximum corrosion rate specifications upon request. Locally high corrosion rates can result in small holes or "pitting" in the metal housing. It has been discovered that a maximum corrosion rate of approximately 1 mil/year is acceptable in most uses both from the standpoint of maintaining the physical integrity of the metallic housing and from the standpoint of maintaining corrosion currents at an acceptable level during operation of the sensor.

The metallic housing members used in the present invention were fabricated from a corrosion resistant metal such as austenitic stainless steel. A number of other metals, including titanium and tantalum, are also suitable.

To facilitate the manufacture of sensors of the present invention, the metal or metals used for the housing also preferably have appropriate physical properties. For example, such metals preferably exhibit an elastic modulus in the range of approximately 191 to approximately 195 gPa (gigapascal). Moreover, such metals preferably exhibit a tensile strength in the range of approximately 500 to approximately 730 mPa. More preferably, the tensile strength is in the range of approximately 580 to approximately 730 mPa. Further, the metals preferably exhibit a yield strength in the range of approximately 260 to approximately 425 mPa.

Figure 2A:
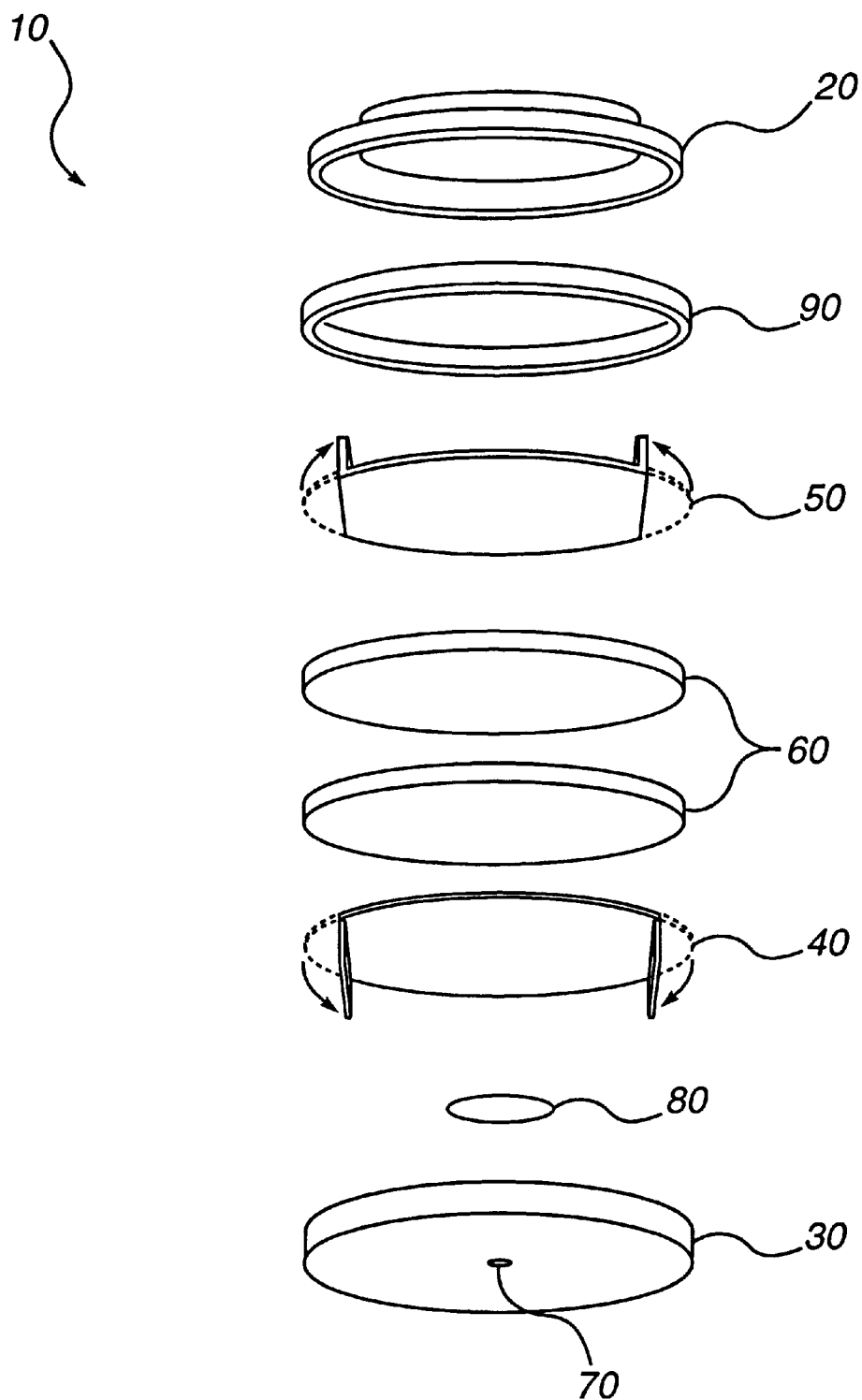
FIG. 2A illustrates an embodiment of an electrochemical sensor of the present invention incorporating a metallic housing.

In the embodiment illustrated in FIG. 2A, the metallic housing comprises a metallic cover 20 and a metallic case 30. Within the enclosure formed by metallic cover 20 and metallic case 30 are placed a working electrode 40, at which the analyte chemically reacts, and a counter electrode 50, at which a reaction complimentary to the reaction occurring at working electrode 40 occurs.

Between working electrode 40 and counter electrode 50, one or more porous wicks 60 are preferably placed. Wicks 60 operate to prevent physical contact of the two electrodes but allow the liquid electrolyte to contact the electrodes and thereby provide ionic conduction and thus an electrical connection between working electrode 40 and counter electrode 50.

Wicks for use in the present invention with an aqueous solution of an acidic electrolyte are preferably fabricated from a hydrophilic material such that the wicks easily absorb and contain the liquid electrolyte (for example, an aqueous, acidic electrolyte such as $H_2SO_4$). The wicks are preferably porous with a percent void volume preferably in the range of approximately 30% to approximately 60%. Additionally, the ratio of the internal volume of the sensor to the void volume of the wicks is preferably in the range of approximately 4 to approximately 12. Void volumes resulting in such an approximate ratio enable the wicks to prevent pressure increases within the sensor associated with intake of water in humid environments from causing leakage of the electrolyte solution from the sensor, while preventing the loss of water from the sensor in dry environments from causing a loss of ionic contact between the electrodes.

Metallic case 30 preferably comprises a sample inlet port 70 through which the analyte may enter during operation of electrochemical sensor 10. Sample inlet port 70 is preferably sealed using a water resistant membrane 80 such as a Gore-Tex® film. In one embodiment, membrane 80 was attached to metallic case 30 via a glue such as a cyanoacrylate glue.

Figure 2B:
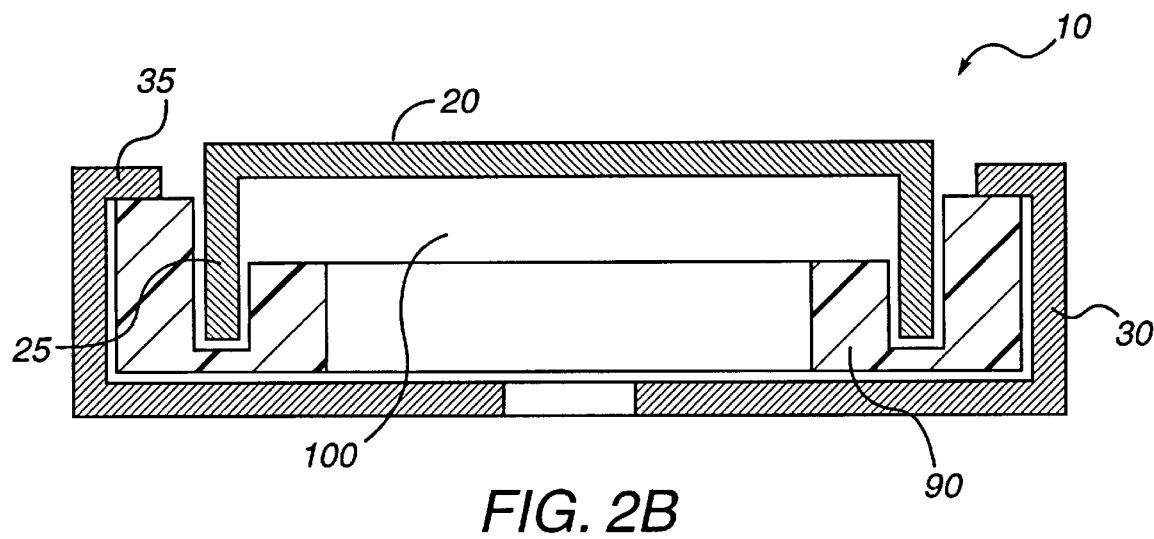
FIG. 2B illustrates in cross-section one embodiment of a substantially sealed enclosure created by metallic housing members of the present invention.

Electrochemical sensor 10 also preferably comprises a sealing member 90, such as an annular plastic grommet, for electrically isolating metallic cover 20 from metallic case 30 and for assisting in providing a secure seal when metallic cover 20 and metallic case 30 are brought together in substantially sealed connection. Such sealing is preferably accomplished by crimping the metallic wall of metallic case 30 as illustrated in FIG. 2B. In the embodiment illustrated in FIG. 2B, sealing member 90 preferably has a U-shaped cross section into which cylindrical side wall 25 of metallic cover 20 fits. Preferably, member 90 and side wall 25 are dimensioned so that a snug fit is achieved. A perimeter portion 35 of metallic case 30 is preferably crimped around member 90 using appropriate mechanical pressure to create a sealed enclosure 100 for housing the electrodes and electrolyte of electrochemical sensor 10.

Preferably, the sealed connection between metallic cover 20 and metallic case 30 is achieved in a manner such that metallic cover 20 is electrically isolated from metallic case 30. This electrical isolation may be achieved, using a sealing member 90 which is electrically insulating, such as the plastic grommet discussed above. Because of the electrical conductivity of metallic cover 20 and metallic case 30, and their electrical isolation from each other, metallic cover 20 can function as the electrical contact for counter electrode 50, and metallic case 30 can function as the electrical contact for working electrode 40.

Figure 2C:
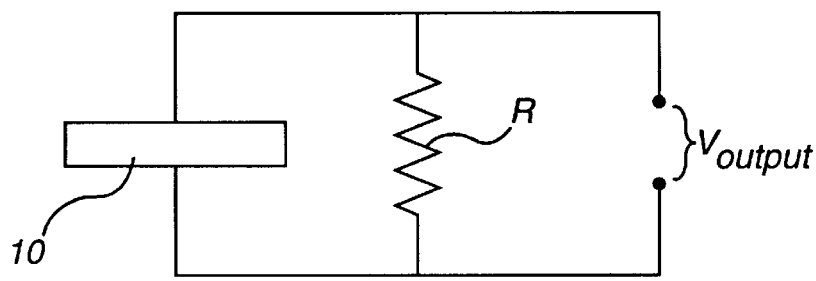
FIG. 2C illustrates an embodiment of a circuit for use with an electrochemical sensor of the present invention showing a resistance load across the sensor (that is, in series electrical connection with the counter and working electrodes).
Figure 2D:
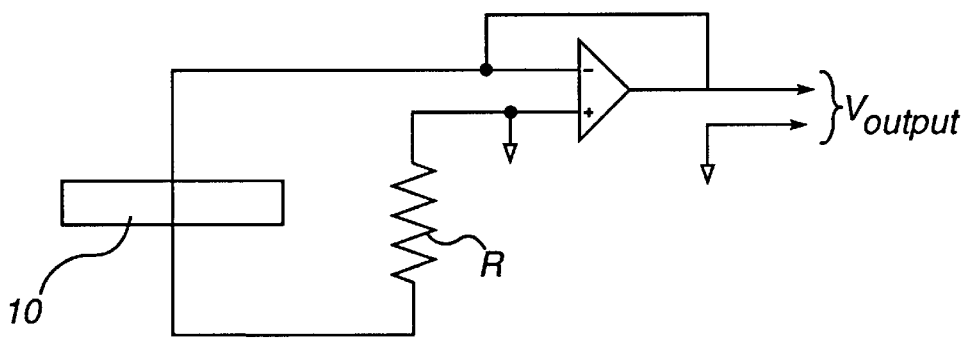
FIG. 2D illustrates another embodiment of a circuit for use with an electrochemical sensor of the present invention.

As illustrated in FIG. 2A, electrical connection between the electrodes and the components of the metallic housing can be accomplished simply by folding working electrode 40 in such a manner that it contacts metallic case 30 and folding counter electrode 50 in such a manner that it contacts metallic cover 20. Alternatively, a separate conductive lead (for example, a stainless steel screen or a Pt lead) can be used to effect such electrical connection. Such contact or lead may, for example, simply abut the metallic case or be spot welded thereto. The use of a load resistance R across electrochemical sensor 10 is illustrated schematically in FIG. 2C. Other output circuits can be used as long as the load resistance R is in series with the counter and working electrodes. See, for example, FIG. 2D.

In fabricating electrodes for use in the present invention, an electrochemically active material (for example, an electrocatalyst) is preferably fixed upon a water resistant membrane such as a Gore-Tex® or Zitex® film as known in the art. Working electrode 40 and counter electrode 50 for use in electrochemical sensor 10 of the present invention can, for example, be fabricated through hand painting or through silk screen deposition of an ink comprising an electrochemically active material. This ink is preferably deposited upon a Gore-Tex film as known in the art. As also known in the art, Gore-Tex films provide a very good support for an electrochemically active material and also provide a good diffusion barrier, allowing analyte (such as gaseous CO) to diffuse into the electrochemical sensor while preventing escape of a liquid acidic electrolyte. Preferably, a film of electrochemically active material having a thickness in the range of approximately 1 to 20 mil is deposited. More preferably, 5 to 15 mil is deposited. As with all electrochemical sensors, a certain degree of selectivity can be achieved and sensor output can be optimized through appropriate choice of electrochemically active materials for use in the electrodes.

While the metallic housings described above may be preferable for the reasons noted above, dose/response curves may be simulated under the present invention using common plastic housings or other housing materials. Further, the results achieved through the increased load of the present invention can be achieved using acidic or caustic electrolytes.

Galvanic CO Sensor Performance Data

The performance of sensors of the present invention has been shown to conform extremely well to the UL specifications over at least the temperature range of 0 to 49° C. set forth in the UL specifications. Although the mechanisms through which electrochemical sensors with the increased load resistances of the present invention operate to approximate dose-response behavior are not completely understood, it is believed that the observed output is a complicated function of the oxidation state of working electrode and/or the capacitance of the working electrode. In metal/air electrodes such as the platinum-black/air electrodes of the present studies, the metal/oxygen ratio changes if the potential of the electrode is changed. Because a large amount of oxygen is generally associated with metal/air electrodes, much current must be drawn to change the electrode potential even slightly. It is believed that in the case of relatively large resistance loads, the current generated by the analyte tends to alter the metal-oxygen ratio slowly and thus slowly change the potential of the electrode. Moreover, in the case of a working electrode having a relatively high surface area and thus relatively high electrical capacitance, it is believed that the change in capacitance experienced by the working electrode is slowed with the use of relatively large resistance loads across the electrochemical sensor. To enable proper adjustment of the response of such sensors, the working electrode preferably has a surface area of at least approximately 1 $m^2/gm$. More preferably, the surface area of the working electrode is at least 10 $m^2/gm$. Most preferably, the surface area of the working electrode is at least 25 $m^2/gm$.

As discussed above, sensor output and response times may be optimized to simulate dose/response curves by appropriate choice of the sensor load resistance. Sensor output and response times in the case of CO sensor comprising a metal housing under various load resistance are set forth in Table 3 below. In these studies standard CR2032 battery casings (as often used in cameras and calculators) were used as the metallic housings. The metallic housings were fabricated from 316 series steel having a wall thickness of approximately 11 mils. The metallic casing were approximately 3.2 mm in height and approximately 20 mm in diameter. Electrodes having diameters in the range of approximately one-half inch or 1.3 cm (apparent area of approximately 1.3 $cm^2$) to approximately five-eighth inch or 1.6 cm (apparent area of approximately 2 $cm^2$) were used in the sensors of the present studies.

TABLE 3

| Load (kΩ) | Output (mV) | $T_{90}$ (mins.) | $T_{80}$ (mins.) | $T_{50}$ (mins.) |
|---|---|---|---|---|
| 1 | −1.24 ± 0.54 | 4.5 | 3.5 | 1.5 |
| 10 | −10.08 ± 3.9 | 34 | 25 | 11 |
| 100 | −32.6 ± 9.4 | 85 | 65 | 31 |

The data of Table 3 above represent the average results from eight sensors tested. A constant CO concentration of 63 ppm at 300 cc/m was used for all loads. Outputs were corrected for zero gas baselines. $T_{90}$, $T_{80}$ and $T_{50}$ represent the times required for the sensor output (mV) to reach 90%, 80% and 50% of the final output, respectively. Further data of sensor output and response times ($T_{90}$) for a second set of eight sensors are set forth in Table 3A.

TABLE 3A

| CO Concentration (ppm) | 100 Ohm Output (mV) | 100 Ohm $T_{90}$ (seconds) | 1 kOhm Output (mV) | 1 kOhm $T_{90}$ (seconds) |
| --- | --- | --- | --- | --- |
| 63 | no measurement taken | no measurement taken | −2.53 ± 0.03 | 337 ± 31 |
| 98 | −0.43 ± 0.03 | 84 ± 37 | −3.92 ± 0.2 | 343 ± 28 |
| 313 | −1.34 ± 0.07 | 90 ± 31 | −11.08 ± 0.51 | 288 ± 26 |
| 594 | −2.26 ± 0.18 | 120 ± 34 | −17.61 ± 1.3 | 206 ± 15 |
| 825 | −3.20 ± 0.18 | 150 ± 24 | −20.3 ± 1.4 | 185 ± 13 |

From the data of Tables 3 and 3A, it is evident that a relatively large resistance of approximately 100 kΩ is preferable to achieve optimum response times with regard to the UL specifications for CO set forth above. Using a 100 kΩ resistor, linearity and response time data were as summarized in Table 4 below. Outputs were for zero gas baselines.

TABLE 4

| [CO], ppm | Output, mV | $T_{90}$, mins. | $T_{80}$, mins. | $T_{50}$, mins. |
| --- | --- | --- | --- | --- |
| 15 | −11 | 150 | 109 | 46 |
| 23 | −21 | 105 | 82 | 39 |
| 53 | −31 | 74 | 57 | 26 |
| 100 | −48 | 73 | 54 | 24 |
| 200 | −61 | 46 | 33 | 15 |
| 290 | −73 | 35 | 26 | 12 |
| 400 | −83 | 31 | 23 | 10 |
| 500 | −86 | 28 | 20 | 9 |

Figure 3:
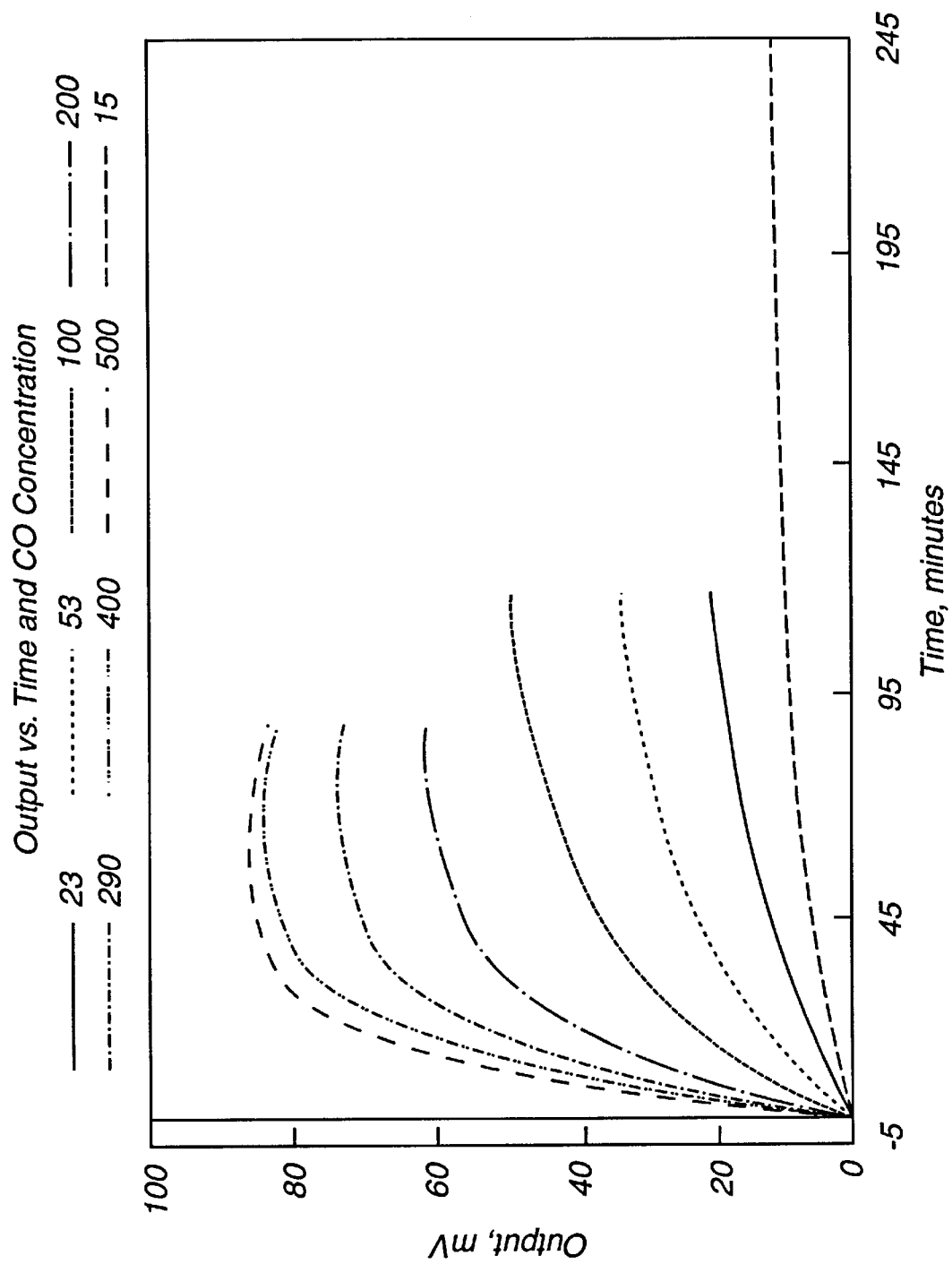
FIG. 3 illustrates sensor output of a CO sensor of the present invention as a function of time for various CO concentrations.

FIG. 3 illustrates sensor output as a function of time for various CO concentrations. From these data it is clear that a CO detector using a sensor of the present invention is easily programmed to respond (for example, by sounding an audible alarm) when the sensor output reaches a predetermined set point value. For the sensor outputs illustrated in FIG. 3, the response times in minutes corresponding to several set points are listed in Table 5. The dashes in Table 5 indicate that the sensors never reached the mV value.

TABLE 5

| [CO], ppm | 20 mV | 30 mV | 40 mV | 50 mV |
| --- | --- | --- | --- | --- |
| 15 | — | — | — | — |
| 23 | 120 | — | — | — |
| 53 | 38 | 90 | — | — |
| 100 | 18 | 34 | 60 | — |
| 200 | 8.33 | 14.33 | 22.33 | 35 |
| 290 | 5.33 | 9 | 13.33 | 19.33 |
| 400 | 4 | 6.33 | 9.66 | 13.66 |
| 500 | 3.33 | 5.33 | 8.33 | 11.33 |

Figure 4:
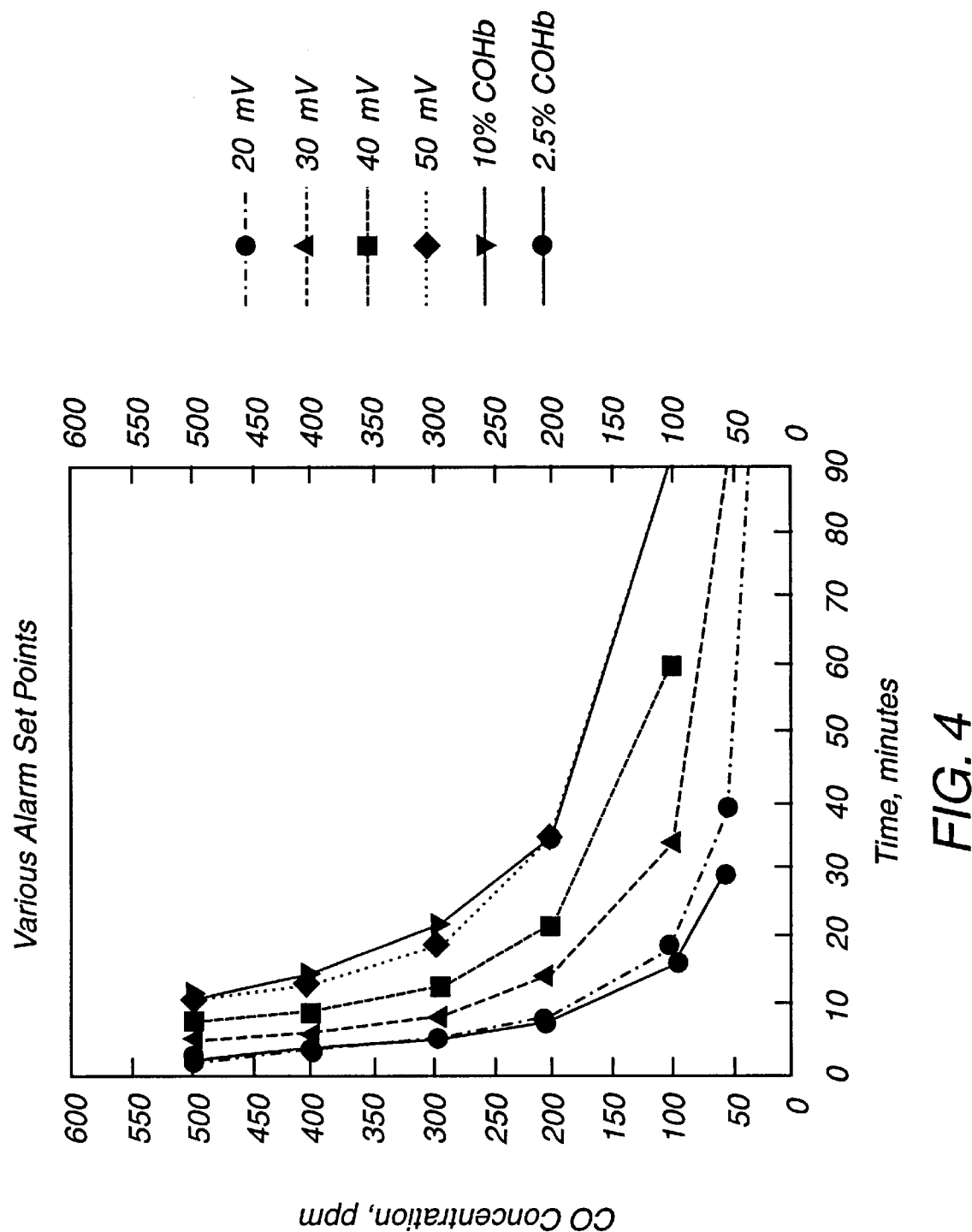
FIG. 4 illustrates graphically and compares the performance of a CO sensor of the present invention to the 10% COHb and 2.5% COHb curves of FIG. 3.

FIG. 4 illustrates the data of Table 5 graphically and compares that data to the 2.5% COHb and 10% COHb curves of FIG. 1. FIG. 4 clearly illustrates that the response of the sensor follows a curve similar in shape to the COHb curves illustrated in FIG. 1. At a 50 mV set point, the detector will never respond to a 100 ppm CO level as required by the UL specification. Therefore, 50 mV is too high for the set point. On the other hand, a 20 mV set point is too low as the response times at that set point approach the minimum response time requirements (that is, the 2.5% COHb curve). However, the set point range of approximately 30 to 40 mV appears to provide extremely good results.

As discussed above, under the UL specifications, a CO detector must include a reset button that silences the alarm when activated. The alarm must resound within five minutes if a CO concentration of 100 ppm or greater is still present in the sample environment. In the sensors of the present invention, sensor output may be temporarily decreased below a predetermined set point by briefly substituting a lower resistance load and subsequently replacing the original resistance load to return to normal function. This temporary substitution first decreases the sensor output below the alarm set point and then (upon replacement of the original resistance load) allows the sensor output to again increase to the alarm set point if a high analyte (for example, CO) concentration remains in the test environment. Studies indicate, for example, that replacing the preferred 100 kΩ resistor in the above-described CO sensor with a 1 kΩ resistor for 30 seconds produces the desired effect. Substituting a resistance load less than 1 kΩ for a period of time shorter than 30 seconds also achieves the required reset effect. Alternately, the required reset effect can be achieved via simple external circuitry, independent of the sensor, as is clear to one skilled in the art.

Galvanic $H_2S$ Sensor Performance

In general, increasing the load resistance across an electrochemical sensor to levels above those commonly used in electrochemical sensors for toxic gases other than CO slows sensor response. By incorporating an appropriate load resistance, a plot of analyte concentration versus response time can be conformed to dose/response curves for such toxic agents. To illustrate this effect, studies were performed with hydrogen sulfide. As was the case for studies with carbon monoxide, standard CR2032 battery casing designs were used for sensor housings. The metallic housings were fabricated from 316 series steel and had the same dimensions describe above for the studies with carbon monoxide. Electrodes having diameters in the range of approximately one-half to five-eighth inch were used. The electrochemically active surface of each of the working electrode and counter electrode comprised iridium (Ir) A 100 kΩ load was applied across the electrochemical sensor.

Figure 5:
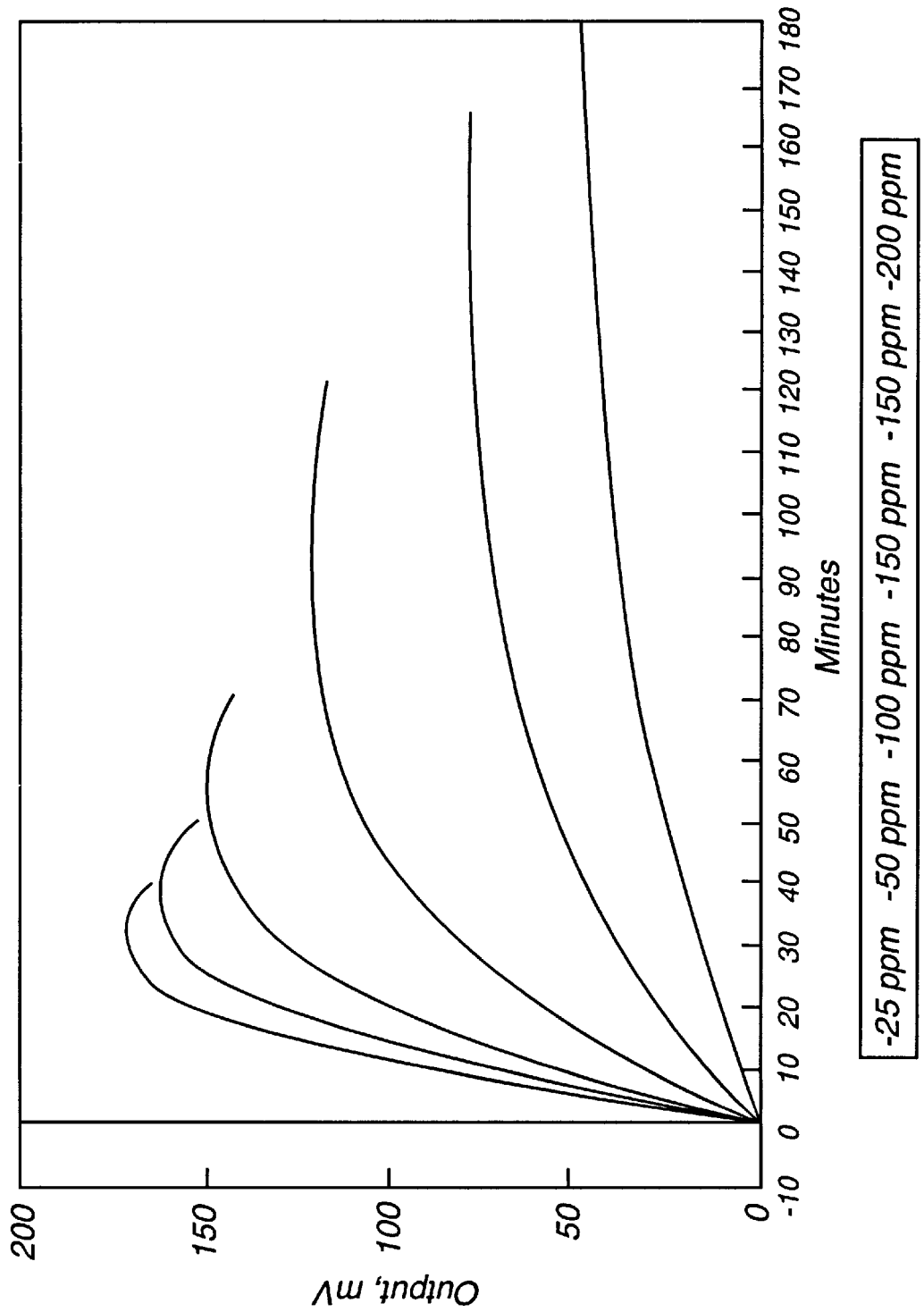
FIG. 5 illustrates sensor output of a hydrogen sulfide ($H_2S$) sensor of the present invention as a function of time for various $H_2S$ concentrations.
Figure 6:
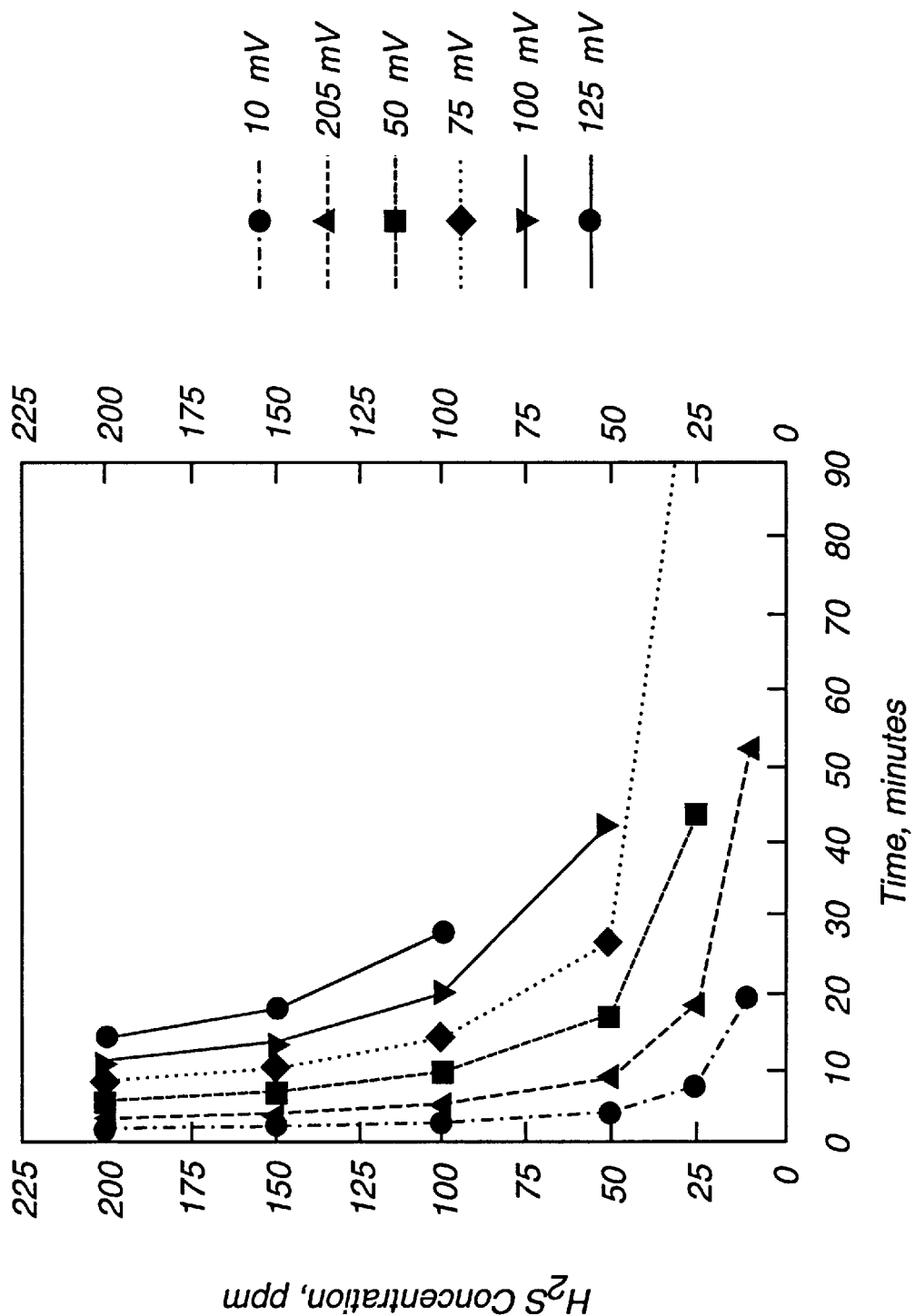
FIG. 6 illustrates graphically the $H_2S$ concentration versus time to reach a set point for various set points.

FIG. 5 illustrates sensor output as a function of time for various $H_2S$ concentrations. The data represented are averages taken from studies with fourteen electrochemical sensors as described above. FIG. 6 illustrates graphically the $H_2S$ concentration versus time to reach a set point for various set points. Clearly, an $H_2S$ detector using a sensor of the present invention is easily programmed to respond when the sensor output reaches a predetermined set point value.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An electrochemical sensor for the detection of an analyte, comprising: a housing, the housing including an inlet therein to allow the analyte to enter the housing, the electrochemical sensor further comprising within the housing a working electrode and a counter electrode, electrical conductivity being maintained between the working electrode and the counter electrode via an electrolyte system present within the housing, the electrochemical sensor further comprising a first resistor in series electrical connection with the working electrode and the counter electrode, the first resistor having a resistance sufficiently high such that an output of the sensor over time at a particular concentration of the analyte approximates the response of a living organism to the analyte over time at the particular concentration.

2. The electrochemical sensor of claim 1 wherein the product of the resistance of the first resistor and the apparent area of the working electrode is at least approximately 1 kΩ·cm².

3. The electrochemical sensor of claim 2 wherein the analyte to be detected is carbon monoxide.

4. The electrochemical sensor of claim 3 wherein the working electrode includes an electrochemically active material comprising platinum and the counter electrode includes an electrochemically active material comprising platinum.

5. The electrochemical sensor of claim 4 wherein the product of the resistance of the resistor and an apparent area of the working electrode is at least approximately 100 k$\Omega$·cm$^2$.

6. The electrochemical sensor of claim 2 wherein the analyte is hydrogen sulfide.

7. The electrochemical sensor of claim 6 wherein the product of the resistance of the first resistor and the apparent area of the working electrode is at least approximately 100 k$\Omega$·cm$^2$.

8. The electrochemical sensor of claim 6 wherein the electrolyte system has a pH less than 3.0.

9. The electrochemical sensor of claim 6 further comprising an alarm mechanism to provide an alarm signal when the output of the electrochemical sensor reaches a predetermined value.

10. The electrochemical sensor of claim 1 wherein the product of the resistance of the first resistor and the apparent area of the working electrode is at least approximately 10 k$\Omega$·cm$^2$.

11. The electrochemical sensor of claim 1 wherein the electrolyte system has a pH less than 3.0.

12. The electrochemical sensor of claim 1 wherein the working electrode is selected from the group consisting of a metal/air electrode and a metal oxide/air electrode.

13. The electrochemical sensor of claim 1 wherein the working electrode has a specific surface of at least 1 m$^2$/gm.

14. The electrochemical sensor of claim 1 further comprising an alarm mechanism to provide an alarm signal when the output of the sensor reaches a predetermined value.

15. The electrochemical sensor of claim 14 further comprising reset circuitry to reset the electrochemical sensor after an alarm is signaled to end the alarm signal and once again allow the electrochemical sensor to detect the analyte.

16. The electrochemical sensor of claim 15 wherein the reset circuitry is adapted to substitute a second resistor having a lower resistance than the first resistor into electrical connection between the first electrode and the second electrode for a period of time.

17. A method of using an electrochemical sensor, the sensor including a housing, the housing including an inlet therein to allow the analyte to enter the housing, the electrochemical sensor further comprising within the housing at least a working electrode and a counter electrode, electrical conductivity being maintained between the working electrode and the counter electrode via an electrolyte system present within the housing, the electrochemical sensor further comprising a first resistor in series electrical connection with the working electrode and the counter electrode, the first resistor having a resistance sufficiently high such that the output of the sensor over time at a particular concentration of an analyte approximates the response of a living organism to the analyte over time at the particular concentration, the method comprising the steps of:

a. placing the electrochemical sensor in communicative connection with an environment containing the analyte such that the analyte can react at the working electrode;

b. measuring the output of the electrochemical sensor to obtain a measurement of the concentration of the analyte in the environment.

18. The method of claim 17 further comprising the step of providing an alarm signal if the output of the electrochemical sensor reaches a predetermined value.

19. The method of claim 18 further comprising the step of resetting the electrochemical sensor after an alarm is signaled to end the alarm signal and once again allow the electrochemical sensor to detect the analyte.

20. The method of claim 19 wherein the step of resetting the electrochemical sensor comprises the step of substituting a second resistor having a lower resistance than the first resistor into electrical connection between the working electrode and the counter electrode for a period of time to reset the electrochemical sensor.

21. An electrochemical sensor for the detection of an analyte, comprising: a housing, the housing including an inlet therein to allow the analyte to enter the housing, the electrochemical sensor further comprising within the housing at least a working electrode and a counter electrode, electrical conductivity being maintained between the working electrode and the counter electrode via an electrolyte system present within the housing, the electrochemical sensor further comprising a first resistor in series electrical connection with the working electrode, the first resistor having a resistance sufficiently high to slow a response of the sensor to approximate the response of a living organism to the analyte over time at the particular concentration.

22. The electrochemical sensor of claim 21 wherein the product of the resistance of the first resistor and the apparent area of the working electrode is at least approximately 1 k$\Omega$·cm$^2$.

23. The electrochemical sensor of claim 22 wherein the analyte to be detected is carbon monoxide.

24. The electrochemical sensor of claim 23 wherein the working electrode includes an electrochemically active material comprising platinum and the counter electrode includes an electrochemically active material comprising platinum.

25. The electrochemical sensor of claim 22 wherein the working electrode has a specific surface of at least 1 m$^2$/gm.

26. The electrochemical sensor of claim 22 wherein the analyte is hydrogen sulfide.

27. The electrochemical sensor of claim 26 wherein the product of the resistance of the first resistor and the apparent area of the working electrode is at least approximately 100 k$\Omega$·cm$^2$.

28. The electrochemical sensor of claim 26 wherein the electrolyte system has a pH less than 3.0.

29. The electrochemical sensor of claim 21 wherein the product of the resistance of the first resistor and the apparent area of the working electrode is at least approximately 10 k$\Omega$·cm$^2$.

30. The electrochemical sensor of claim 21 wherein the product of the resistance of the resistor and an apparent area of the working electrode is at least approximately 100 k$\Omega$·cm$^2$.

31. The electrochemical sensor of claim 21 wherein the electrolyte system has a pH less than 3.0.

32. The electrochemical sensor of claim 21 wherein the working electrode is a metal/air electrode or a metal oxide/air electrode.

33. The electrochemical sensor of claim 21 further comprising an alarm mechanism to provide an alarm signal when an output of the sensor reaches a predetermined value.

34. The electrochemical sensor of claim 33 further comprising reset circuitry to reset the electrochemical sensor after an alarm is signaled to end the alarm signal and once again allow the electrochemical sensor to detect the analyte.

35. The electrochemical sensor of claim 34 wherein the reset circuitry is adapted to substitute a second resistor having a lower resistance than the first resistor into series electrical connection with the working electrode for a period of time.

* * * * *